United States Patent [19]
Traue et al.

[11] Patent Number: 5,900,412
[45] Date of Patent: May 4, 1999

[54] PERCUTANEOUS/TRANSDERMAL DELIVERY OF ASA AND ANTITHROMBOTIC THERAPIES BASED THEREON

[75] Inventors: Jürgen Traue, Munich; Andreas Teubner, Pfaffenhofen; Elmar Wadenstorfer, Munich, all of Germany

[73] Assignee: Luitpold Pharma GmbH, Munich, Germany

[21] Appl. No.: 08/845,386

[22] Filed: Apr. 25, 1997

[30] Foreign Application Priority Data

Apr. 25, 1996 [DE] Germany .............................. 196 16 539

[51] Int. Cl.$^6$ ...................................................... A61K 31/60
[52] U.S. Cl. ............................ 514/165; 514/822; 514/946
[58] Field of Search ..................................... 514/165, 822, 514/946

[56] References Cited

FOREIGN PATENT DOCUMENTS

| | | |
|---|---|---|
| 0069385 A2 | 1/1983 | European Pat. Off. . |
| 0147146 A2 | 7/1985 | European Pat. Off. . |
| 0513832 A1 | 11/1992 | European Pat. Off. . |
| 0581587 A2 | 2/1994 | European Pat. Off. . |
| 3413052 A1 | 12/1984 | Germany . |
| 92/20343 | 11/1992 | WIPO . |
| 94/13302 | 6/1994 | WIPO . |
| 96/30000 | 10/1996 | WIPO . |
| 97/04759 | 2/1997 | WIPO . |

*Primary Examiner*—Kimberly Jordan
*Attorney, Agent, or Firm*—Burns, Doane, Swecker & Mathis, L.L.P.

[57] ABSTRACT

Topically applicable pharmaceutical/therapeutic alcoholic solution compositions, well suited for percutaneous/transdermal antithrombotic therapy, comprise an effective antithrombotic amount of acetylsalicylic acid ("ASA") or salt thereof, formulated into primary alcohol (e.g., isopropanol) and secondary ester (e.g., isopropyl myristate) solvents therefor, optionally in the presence of penetration enhancers and/or ASA hydrolysis inhibitors.

22 Claims, 1 Drawing Sheet

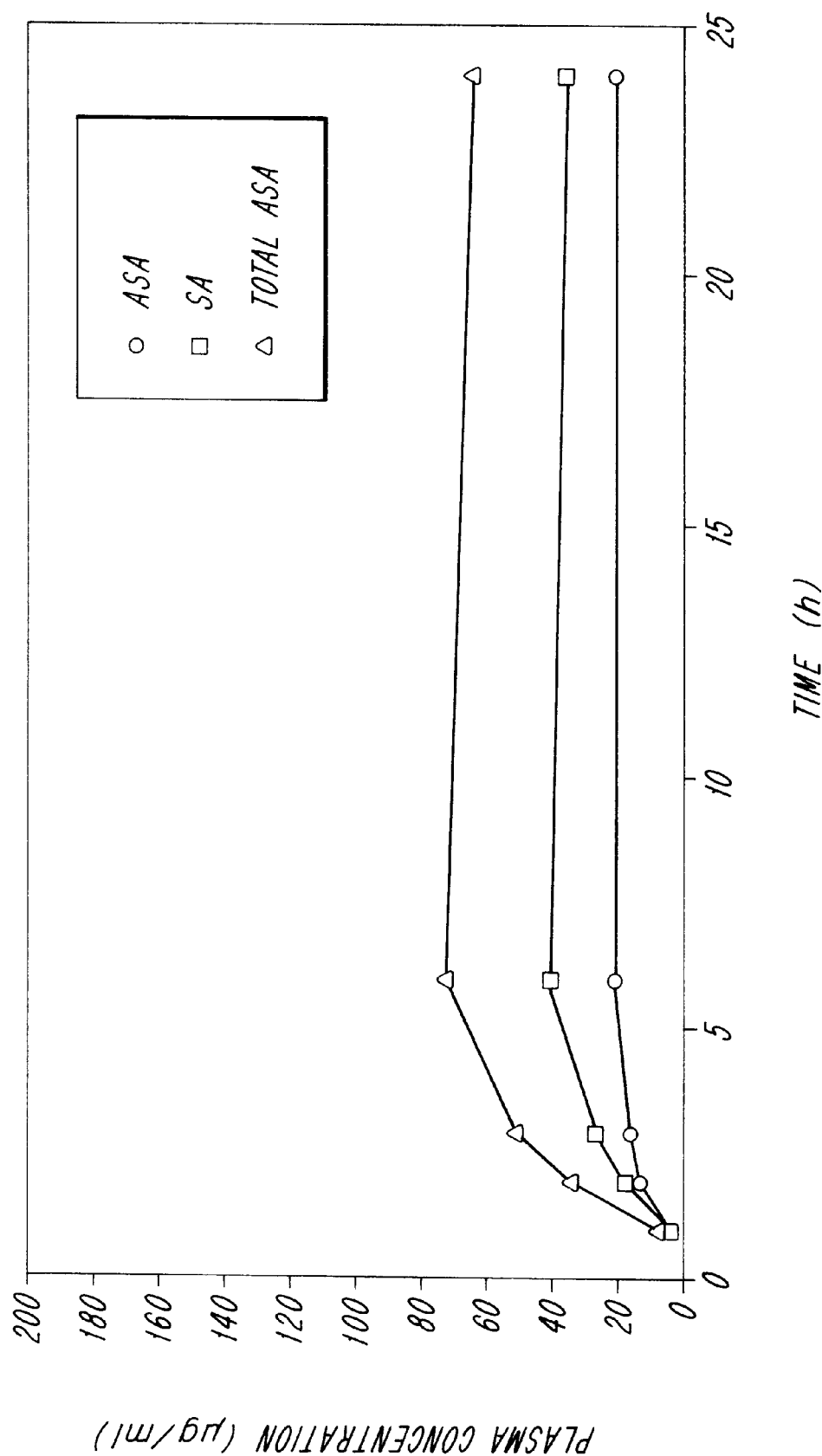

PERCUTANEOUS/TRANSDERMAL DELIVERY OF ASA AND ANTITHROMBOTIC THERAPIES BASED THEREON

BACKGROUND OF THE INVENTION

1. Technical Field of the Invention

The present invention relates to novel pharmaceutical preparations of acetylsalicylic acid comprising alcoholic solutions thereof and to percutaneous antithrombotic applications of such novel compositions.

2. Description of the Prior Art

Acetylsalicylic acid (ofttimes "ASA" below) has hitherto principally been administered orally. In the medical arts, ASA is primarily indicated as a nonsteroidal anti-inflammatory drug (NSAID), eliciting anti-inflammatory, analgesic and antipyretic effects. In addition to these, ASA elicits other effects, such as inhibition of thrombocyte aggregation, and is therefore employed in long-term therapy, particularly for reinfarction prophylaxis of cerebral and cardiac infarctions. For this purpose, it has also been administered via the peroral route.

ASA (but not salicylic acid ("SA" below)) causes irreversible acetylation, and consequently prolonged inactivation, of cyclooxygenase. For the blood platelets, which lack a nucleus and which, in contrast to other tissues, cannot replace the cyclooxygenase by fresh synthesis, this irreversible inhibition at the same time indicates inhibition of the synthesis of the proaggregating agent thromboxane for the entire life of the thrombocytes (1 month).

For this reason, it is only ASA, and not its hydrolysis product SA, which exhibits antithrombotic activity.

The requisite dose for preventing thromboembolic complications still has not been finally determined: at present, daily doses of 30–500 mg are recommended, depending on the indication, with the low-dose therapy exhibiting fewer side effects (V. Fuster et al., *Circulation*, 87, 659–675 (1993)).

ASA is rapidly metabolized to its principal metabolite SA in the gastrointestinal fluids, during absorption in the stomach and intestine and in the blood plasma. Due to the presystemic metabolism, the absolute bio-availability of ASA following peroral administration is only approximately 50%–70% (H. Blume and E. Mutschler, "Bio äquivalenz—Qualitätsbewertung wirkstoffgleicher Fertigarzneimittel [Bioequivalence—quality assessment of finished drugs containing the same active compound]," *Govi Verlag*, 2nd Supplementary Fascicle 1991, acetylsalicylic acid).

The transdermal administration of ASA, which has long been proposed, is particularly advantageous for antithrombotic therapy since, under these circumstances, the ASA is administered systemically, thereby circumventing the gastrointestinal tract.

To date, oral administration has been practised almost exclusively when using ASA for antithrombotic therapies.

Active compound-containing ointments, creams or gels are employed when administering ASA for the local therapy of diseases of the skin or for the treatment of pain, inflammation and/or rheumatic diseases.

The following alternatives have been disclosed for this purpose:

FR-A-7,502,651 describes solutions of ASA in ethanol for the transcutaneous treatment of pain. These ethanolic solutions are, however, incorporated into creams or ointments. Absorption data are not provided.

U.S. Pat. No. 4,219,548 describes alcoholic solutions of ASA which comprise glycerol monooleate and a glycol. ASA is present in concentrations of from 0.5% to 10%. The solutions are suitable for the topical treatment of inflamed tissue. The symptoms which are described as being treatable are essentially skin inflammations (acne).

U.S. Pat. No. 4,460,368 describes a transdermal system ("TDS" below) for administering ASA, in which the ASA is contained in aqueous solution together with solubilizers. No data are provided with regard to the stability of ASA in the formulation or with regard to plasma levels. Pain and inflammation are the indications for the ASA TDS.

EP-A-0,581,587 describes an excipient for the transdermal administration of various pharmaceutically active compounds, including aspirin (=acetylsalicylic acid) as an anti-inflammatory active compound. The excipient obligatorily consists of the three components, fatty acid ester, alcohol and water.

DE-A-3,413,052 and U.S. Pat. No. 4,665,063 describe topical formulations for the treatment of inflammatory dermatological diseases, including alcoholic solutions of ASA in concentrations of >7%. Several solutions were tested on patients suffering from skin diseases, but no data are provided on the absorption of ASA.

The following alternatives have been disclosed or the transdermal administration of acetylsalicylic acid for thrombosis therapy:

WO 92/20343 describes alcoholic ASA solutions for transdermal thrombosis therapy, which solutions comprise propylene glycol as the essential constituent. A slow and slight transcutaneous absorption of the active compound following topical applications is intended.

DE-A-4,241,128 and WO 94/13302 describe ASA plasters for thrombosis treatment. The employment of TDS for long-term use is described without there existing any data on the absorption of the active compound or on the tolerability of such ASA plasters on the skin.

SUMMARY OF THE INVENTION

It has now surprisingly and unexpectedly been determined that ASA is absorbed rapidly and satisfactorily from alcoholic solutions which comprise a suitable secondary solvent.

Briefly, the present invention features novel alcoholic solutions for the percutaneous administration of ASA, comprising acetylsalicylic acid or salts thereof as the active compound, a monohydric aliphatic $C_2$–$C_4$ alcohol as the primary solvent and an ester of a monohydric aliphatic $C_2$–$C_6$ alcohol with an aliphatic $C_{12}$–$C_{16}$ monocarboxylic acid, or with an aliphatic $C_4$–$C_8$ dicarboxylic acid, as the secondary solvent and also, where appropriate, optionally a cyclic terpene as a penetration enhancer and/or acetic anhydride as a hydrolysis inhibitor.

The novel solutions according to the invention can be administered both directly and also when formulated into a suitable vehicle, diluent or carrier therefor.

BRIEF DESCRIPTION OF THE DRAWING

The FIGURE of Drawing is a graph plotting plasma concentrations of ASA, SA and total active compound (as total ASA) over time, following cutaneous application of an ASA composition of the present invention onto the backs of rabbits.

DETAILED DESCRIPTION OF BEST MODE AND SPECIFIC/PREFERRED EMBODIMENTS OF THE INVENTION

More particularly according to the present invention, the primary solvent having good dissolution properties for the formulation constituents should be readily volatile, whereas the secondary solvent must not be volatile in order to ensure that the active compound is maintained in dissolved state on and in the skin.

Monohydric aliphatic $C_2$–$C_4$ alcohols (in particular saturated $C_2$–$C_4$ alcohols), such as ethanol, propanol, isopropanol, 1-butanol and 2-butanol, are suitable primary solvents for the subject novel alcoholic solutions, with propanol and isopropanol being preferred. Isopropanol is very particularly preferred. The proportion of the primary solvent in the formulation can vary and advantageously ranges from 10% to 90%, with from 25% to 65% being preferred.

Here, and in the description which follows, percentage values denote, unless otherwise indicated, percent by weight and are based on the finished solution.

Exemplary secondary solvents include the esters of aliphatic saturated or unsaturated $C_{12}$–$C_{16}$, monocarboxylic acids, such as lauric acid, myristic acid and palmitic acid, with myristic acid being preferred, with monohydric aliphatic $C_2$–$C_6$ alcohols, such as ethanol, isopropanol, isobutanol, pentyl alcohol and hexyl alcohol, with ethanol and isopropanol being preferred. Isopropyl myristate is particularly preferred.

Suitable secondary solvents also include the esters of aliphatic $C_4$–$C_8$ dicarboxylic acids, such as succinic acid, glutaric acid, adipic acid or pimelic acid, with adipic acid being preferred, with monohydric aliphatic $C_2$–$C_6$ alcohols, such as isopropanol, butanol, pentanol and hexanol, with butanol being preferred. Butyl adipate is particularly preferred.

The proportion by weight of the secondary solvent in the formulation can vary and advantageously ranges from 10% to 80% by weight, with a range of from 20% to 60% by weight being preferred.

Esters of said dicarboxylic acids with monohydric aliphatic $C_7$–$C_{18}$ alcohols, such as heptanol, octanol, decanol, lauryl alcohol, myristyl alcohol and palmityl alcohol, are also suitable secondary solvents.

Where appropriate, penetration enhancers of the cyclic terpene type, preferably L-menthol or thymol, may be present in the subject alcoholic solutions. The proportion by weight of the penetration enhancers advantageously ranges from 0.1% to 5%, preferably from 0.5% to 2% by weight.

Also where appropriate, acetic anhydride may be present in the subject solutions in order to prevent hydrolysis of the active compound ASA. When present, the acetic anhydride is preferably at a concentration of from 0.001% to 0.15% by weight.

The active compound ASA is advantageously present in the subject alcoholic solutions in concentrations of from 1% to 15%, preferably from 5% to 15%, and more preferably about 10% by weight.

For administration, the alcoholic ASA solutions may be formulated into a suitable vehicle, diluent or carrier therefor, or else topically applied directly to the skin.

As above indicated, penetration of the ASA using the novel alcoholic ASA solutions of the invention is unexpectedly superior to that attained using the pharmaceutical preparations described in WO-92/20343. In addition, significant levels of ASA are attained in the plasma using the novel alcoholic solutions according to the present invention.

In order to further illustrate the present invention and the advantages thereof, the following specific examples are given, it being understood that same are intended only as illustrative and in nowise limitative.

EXAMPLE 1

1 kg of ASA was dissolved in a mixture of 3.2 kg of isopropanol and 5.8 kg of butyl adipate (Cetiol B) and, after having been clarified by filtration, the solution was introduced into 200 screw-neck bottles fitted with atomizers.

EXAMPLE 2

1 kg of ASA was dissolved in a mixture of 4.5 kg of isopropanol and 4.5 kg of butyl adipate (Cetiol B) and, after having been clarified by filtration, the solution was introduced into 200 screw-neck bottles fitted with atomizers.

EXAMPLE 3

1 kg of ASA and 0.1 kg of L-menthol were dissolved in a mixture of 3.15 kg of isopropanol and 5.75 kg of butyl adipate (Cetiol B). 10 g of acetic anhydride were added to the solution. After having been clarified by filtration, the solution was introduced into 200 screw-neck bottles fitted with atomizers.

EXAMPLE 4

1.2 kg of ASA were dissolved in a mixture of 6.45 kg of isopropanol and 2.35 kg of isopropyl myristate and, after having been clarified by filtration, the solution was introduced into 200 screw-neck bottles fitted with atomizers.

EXAMPLE 5

1.2 kg of ASA were dissolved in a mixture of 4.8 kg of isopropanol and 4.5 kg of isopropyl myristate and, after having been clarified by filtration, the solution was introduced into 200 screw-neck bottles fitted with atomizers.

EXAMPLE 6

1 kg of ASA was dissolved in a mixture of 5 kg of isopropanol and 4 kg of Cetiol B and, after having been clarified by filtration, the solution was introduced into 200 screw-neck bottles fitted with atomizers.

EXAMPLE 7

1 kg of ASA was dissolved in a mixture of 4.9 kg of isopropanol and 4 kg of isopropyl adipate (Cremogen IP). 0.1 kg of L-menthol was added to the solution. After having been clarified by filtration, the solution was introduced into 200 screw-neck bottles fitted with atomizers.

Investigations employing the mouse-skin absorption model (MSA model):

Approximately 500.0 mg of the subject ASA solutions were in each case topically applied to excised nude-mouse skin which was mounted in a Franz diffusion cell. At the specified times, the content of active compound in the acceptor medium buffer, pH 7.2, was determined by means of HPLC analysis, thereby enabling the active compound flux to be calculated in $\mu g/cm^2 \times h$.

The formulations of 10% ASA in propylene glycol/isopropanol (1.7/1), formulation A, and propylene glycol/ethanol (1.7/1), formulation B, which are described in WO 92/20343 were tested for purposes of comparison. In the investigations, it was observed, surprisingly, that the acetylsalicylic acid was absorbed through the skin substantially more rapidly, and for a considerably longer period of time, from the novel preparation which was prepared in accordance with Example 1 than after applying the 10% solutions of ASA in the comparison formulations described in WO 92/20343.

It was possible to adjust the proportions of the primary solvent and the secondary solvent to regulate the flux of ASA through the mouse skin. The further addition of menthol to the alcoholic solution of ASA according to the invention, in conformity with Example 3, resulted in a further marked improvement in ASA penetration.

The alcoholic solution according to Example 4 containing isopropyl myristate (designated "IPM" below) as the secondary solvent also produced a substantially higher flux of ASA than did the comparison formulations.

The results obtained are reported in the following Table:

TABLE

Total ASA flux in the mouse-skin absorption model
following application of ASA solutions:

| ASA formulation from Example | Total ASA flux in $\mu g/cm^2 \times h$ after an experiment duration of (h) | | | |
|---|---|---|---|---|
| | 2 | 3 | 4 | 6 |
| 1 | | 182 | | 252 |
| 3 | | 451 | | 599 |
| 4 | 977 | | 1416 | 1066 |
| Comparison (A) WO 92/20343 | | 9 | | 20 |
| Comparison (B) WO 92/20343 | | 8 | | 31 |

Testing the absorption of ASA in rabbits: Cutaneous application of the ASA solution from Example 1 (100 mg of ASA kg):

ASA was present in the plasma of two of the animals at one hour after topically applying the 10% solution of ASA of Example 1 to the backs of 5 rabbits, and was present in the plasma of all of the animals investigated at two hours after application. Conditioned by the cutaneous absorption of the active compound, the plasma level of ASA slowly increased during the first 6 hours of the experiment to approximately 20 $\mu g/ml$.

The sum of the concentrations of ASA and SA, calculated as ASA, was a measure of the total amount of absorbed ASA. After six hours, this total ASA plasma level was 75 $\mu g/ml$.

With a slight delay, the plasma levels of the metabolite SA were present, from the second hour and thereafter to be in each case comparable to or higher than those of ASA—with the concentration of SA being at most twice that of ASA.

A relatively high concentration of ASA, of approximately 20 $\mu g/ml$, was still present even 24 hours after the cutaneous application, evidencing a relatively long-lasting absorption of ASA from a skin depot.

These results are shown in the FIGURE of Drawing.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable pharmaceutical/therapeutic alcoholic solution composition suited for percutaneous/transdermal antithrombotic therapy, which consists essentially of an effective antithrombotic amount of acetylsalicylic acid (ASA) or salt thereof, a monohydric aliphatic $C_2$–$C_4$ alcohol as a primary solvent, an ester of a monohydric aliphatic $C_2$–$C_6$ alcohol with an aliphatic $C_{12}$–$C_{16}$ monocarboxylic acid or an ester of a monohydric aliphatic $C_2$–$C_6$ alcohol with an aliphatic $C_4$–$C_8$ dicarboxylic acid as a secondary solvent, and optionally at least one of a percutaneous/transdermal penetration enhancer and an ASA hydrolysis inhibitor.

2. The alcoholic solution composition as defined by claim 1, wherein said penetration enhancer is a cyclic terpene compound and said hydrolysis inhibitor is acetic anhydride.

3. The alcoholic solution composition as defined by claim 2, which contains from 0.1% to 5% by weight of L-menthol and/or thymol and/or from 0.001% to 0.15% by weight of acetic anhydride.

4. A method for treating thrombosis in a mammalian organism in need of such treatment, comprising topically applying thereto an antithrombotically and percutaneous delivery effective amount of the alcoholic solution composition as defined by claim 2.

5. The alcoholic solution composition as defined by claim 1, further consisting essentiallly of a topically pharmaceutically/therapeutically acceptable vehicle, diluent or carrier therefor.

6. A method for treating thrombosis in a mammalian organism in need of such treatment, comprising topically applying thereto an antithrombotically and percutaneous delivery effective amount of the alcoholic solution composition as defined by claim 5.

7. The alcoholic solution composition as defined by claim 1, which contains a volatile primary alcohol solvent and a nonvolatile secondary ester solvent.

8. The alcoholic solution composition as defined by claim 1, wherein said primary alcohol solvent is ethanol, propanol, isopropanol, 1-butanol or 2-butanol.

9. The alcoholic solution composition as defined by claim 8, wherein said primary alcohol solvent is isopropanol.

10. The alcoholic solution composition as defined by claim 8, wherein said secondary solvent is an ester of lauric, myristic or palmitic acid with ethanol, isopropanol, isobutanol, pentyl alcohol or hexyl alcohol.

11. The alcoholic solution composition as defined by claim 10, wherein said secondary ester solvent is isopropyl myristate.

12. The alcoholic solution composition as defined by claim 8, wherein said secondary solvent is an ester of succinic, glutaric, adipic or pimelic acid with isopropanol, butanol, pentanol or hexanol.

13. The alcoholic solution composition as defined by claim 12, wherein said secondary ester solvent is butyl adipate.

14. The alcoholic solution composition as defined by claim 8, wherein said secondary solvent is an ester of heptanol, octanol, decanol, lauryl alcohol, myristyl alcohol or palmityl alcohol with said aliphatic $C_4$–$C_8$ dicarboxylic acid.

15. The alcoholic solution composition as defined by claim 1, which contains from 10% to 90% by weight of said primary alcohol solvent.

16. The alcoholic solution composition as defined by claim 15, which contains from 10% to 80% by weight of said secondary ester solvent.

17. The alcoholic solution composition as defined by claim 16, which contains from 1% to 15% by weight of said ASA or salt thereof.

18. The alcoholic solution composition as defined by claim 17, which contains from 5% to 15% by weight of said ASA or salt thereof.

19. The alcoholic solution composition as defined by claim 18, which contains about 10% by weight of said ASA or salt thereof.

20. The alcoholic solution composition as defined by claim 15, which contains from 25% to 65% by weight of said primary alcohol solvent.

21. The alcoholic solution composition as defined by claim 20, which contains from 20% to 60% by weight of said secondary ester solvent.

22. A method for treating thrombosis in a mammalian organism in need of such treatment, comprising topically applying thereto an antithrombotically and percutaneous delivery effective amount of the alcoholic solution composition as defined by claim 1.

* * * * *